US009931641B2

(12) United States Patent
Chan et al.

(10) Patent No.: US 9,931,641 B2
(45) Date of Patent: Apr. 3, 2018

(54) AIR PURIFICATION DEVICE AND METHOD (75) Inventors: Yiu Wai Chan, Hong Kong (HK); Sui Chun Law, Hong Kong (HK); Yiu Ming Chan, Hong Kong (HK)

(73) Assignee: Yiu Ming Chan, Hong Kong (HK)

( * ) Notice: Subject to any disclaimer, the term of this patent is extended or adjusted under 35 U.S.C. 154(b) by 0 days.

(21) Appl. No.: 13/489,582

(22) Filed: Jun. 6, 2012

(65) Prior Publication Data
US 2012/0312169 A1   Dec. 13, 2012

(30) Foreign Application Priority Data
Jun. 7, 2011   (HK) .................... 11105631

(51) Int. Cl.
B03C 3/36 (2006.01)
B03C 3/08 (2006.01)
B03C 3/145 (2006.01)
B03C 3/47 (2006.01)
B01D 53/32 (2006.01)
A61L 9/16 (2006.01)

(52) U.S. Cl.
CPC ............ *B03C 3/363* (2013.01); *B01D 53/323* (2013.01); *B03C 3/08* (2013.01); *B03C 3/145* (2013.01); *B03C 3/365* (2013.01); *B03C 3/366* (2013.01); *B03C 3/47* (2013.01); *A61L 9/16* (2013.01); *A61L 2209/14* (2013.01); *A61L 2209/16* (2013.01); *B01D 2258/06* (2013.01); *B03C 2201/18* (2013.01); *Y02A 50/2357* (2018.01)

(58) Field of Classification Search
CPC .............. B03C 3/145; B03C 3/47; B03C 3/51

USPC ...................................... 96/54, 100
See application file for complete search history.

(56) References Cited

U.S. PATENT DOCUMENTS

| | | | | |
|---|---|---|---|---|
| 1,956,591 A | * | 5/1934 | Gies ......................... | B03C 3/51 55/440 |
| 2,397,197 A | * | 3/1946 | Newman ........................... | 96/58 |
| 2,479,625 A | * | 8/1949 | Kimmell ............... | B01D 45/08 55/440 |
| 2,640,194 A | * | 5/1953 | Hytte ...................... | F28F 3/042 138/38 |
| 2,700,429 A | * | 1/1955 | Wintermute ............. | B03C 3/36 55/DIG. 31 |
| 2,711,226 A | * | 6/1955 | Davis, Jr. ................. | B03C 3/15 96/61 |
| 2,841,238 A | * | 7/1958 | Lenehan .................. | B03C 3/16 261/112.1 |

(Continued)

Primary Examiner — Amber R Orlando
Assistant Examiner — Stephen Hobson
(74) Attorney, Agent, or Firm — Muncy, Geissler, Olds & Lowe, P.C.

(57) ABSTRACT

The present invention is an air purification method and device. Due to the lower airflow resistance that the present invention induces, an exhaust fan or blower with motor of lower torque is adopted. Consequently, the whole air purification is operated at a lower noise level. Lower operational voltage is applicable for the high-voltage electrostatic precipitator device and provides a similar or superior performance and effectiveness for dust removal. The air purification device/system is designed with higher flexibility and of more compact in dimension and size. Dust is removed from the environment by a high voltage electrostatic precipitator. The airflow stream within a high-voltage electrostatic precipitator is such that the direction of the path of the airflow is changed at least twice.

16 Claims, 4 Drawing Sheets (56) References Cited

U.S. PATENT DOCUMENTS

| | | | | |
|---|---|---|---|---|
| 2,903,089 A * | 9/1959 | Latham, Jr. | B03C 3/15 | 96/61 |
| 3,149,936 A * | 9/1964 | Rich | B03C 3/743 | 96/40 |
| 3,338,035 A * | 8/1967 | Dinkelacker | B01D 45/08 | 55/440 |
| 3,517,486 A * | 6/1970 | Golden | B01D 45/08 | 55/394 |
| 3,761,062 A * | 9/1973 | King | F02M 27/04 | 123/536 |
| 3,765,154 A * | 10/1973 | Hardt et al. | | 96/88 |
| 3,844,741 A * | 10/1974 | Dimitrik | B01D 53/0407 | 250/431 |
| 3,849,090 A * | 11/1974 | Remick | | 96/86 |
| 3,849,095 A * | 11/1974 | Regehr | B01D 45/08 | 55/394 |
| 3,870,488 A * | 3/1975 | Arndt | B01D 45/08 | 55/440 |
| 3,925,040 A * | 12/1975 | Fattinger | B01D 45/16 | 261/108 |
| 3,950,153 A * | 4/1976 | Von Berckheim | B03C 3/51 | 96/78 |
| 3,958,958 A * | 5/1976 | Klugman | B03C 3/16 | 261/98 |
| 3,976,448 A * | 8/1976 | Eng | B01D 49/00 | 123/572 |
| 4,074,983 A * | 2/1978 | Bakke | B03C 3/01 | 96/47 |
| 4,116,789 A * | 9/1978 | King | B03C 3/36 | 204/545 |
| 4,175,938 A * | 11/1979 | Regehr | B01D 45/16 | 55/440 |
| 4,218,408 A * | 8/1980 | Henning | F28F 25/087 | 261/112.2 |
| 4,272,462 A * | 6/1981 | Butt | F28D 5/02 | 165/166 |
| 4,289,504 A * | 9/1981 | Scholes | B03C 3/017 | 95/73 |
| 4,478,614 A * | 10/1984 | Jonelis | B03C 3/86 | 96/87 |
| 4,529,418 A * | 7/1985 | Reif | B03C 3/53 | 261/112.1 |
| 4,735,633 A * | 4/1988 | Chiu | B01D 53/00 | 118/723 E |
| 4,774,033 A * | 9/1988 | Raybon | B01J 19/32 | 261/109 |
| 4,802,901 A * | 2/1989 | Wurz | B01D 45/06 | 261/DIG. 11 |
| 4,844,718 A * | 7/1989 | Schmidt | B03C 3/74 | 95/26 |
| 4,919,696 A * | 4/1990 | Higashi | B01D 47/06 | 55/434.4 |
| 5,017,203 A * | 5/1991 | Cox | B01D 47/06 | 55/457 |
| 5,037,456 A * | 8/1991 | Yu | B03C 3/12 | 96/76 |
| 5,104,431 A * | 4/1992 | Fewel, Jr. | B01D 45/08 | 55/440 |
| 5,269,823 A * | 12/1993 | Wurz | B01D 45/16 | 55/440 |
| 5,591,253 A * | 1/1997 | Altman et al. | | 96/61 |
| 5,695,549 A * | 12/1997 | Feldman | B03C 3/0175 | 95/80 |
| 5,729,564 A * | 3/1998 | Cullumber | H01S 3/036 | 372/34 |
| 5,922,111 A * | 7/1999 | Omi | B03C 3/025 | 55/DIG. 38 |
| 5,972,062 A * | 10/1999 | Zimmermann | B01D 45/08 | 55/440 |
| 6,149,697 A * | 11/2000 | Dullien | B01D 45/02 | 55/308 |
| 6,260,830 B1 * | 7/2001 | Harrison | F28C 1/04 | 261/112.2 |
| 6,770,121 B1 * | 8/2004 | Sindel | B01D 45/08 | 55/435 |
| 6,962,620 B2 * | 11/2005 | Chang | B03C 3/32 | 96/60 |
| 7,811,343 B2 * | 10/2010 | Toma | B01D 45/08 | 55/318 |
| 8,268,058 B2 * | 9/2012 | Wu | B03C 3/09 | 95/78 |
| 8,454,733 B2 * | 6/2013 | Tanaka | B03C 3/08 | 96/77 |
| 8,574,353 B2 * | 11/2013 | Nazuka | B03C 3/09 | 96/62 |
| 8,899,557 B2 * | 12/2014 | Cullinane | B01D 19/0036 | 261/76 |
| 2008/0194009 A1 * | 8/2008 | Marentis | A61L 9/14 | 435/283.1 |
| 2008/0250926 A1 * | 10/2008 | Riskin | B03C 3/06 | 95/57 |
| 2009/0255816 A1 * | 10/2009 | Tryti | B01D 17/06 | 204/672 |
| 2011/0209620 A1 * | 9/2011 | Nazuka | B03C 3/09 | 96/62 |
| 2012/0073666 A1 * | 3/2012 | Hjelmberg | B01D 53/86 | 137/1 |
| 2015/0266032 A1 * | 9/2015 | Zhou | B03C 3/0175 | 96/53 |

* cited by examiner

AIR PURIFICATION DEVICE AND METHOD

This nonprovisional application claims priority under 35 U.S.C. § 119(a) to Hong Kong short term patent application No. 11105631.1, which was filed in Hong Kong on Jun. 7, 2011, and which is herein incorporated by reference.

FIELD OF THE INVENTION

This invention concerns an intelligent apparatus for air purification.

TECHNICAL BACKGROUND

The air pollutants exist in two major physical phases: particle phase pollutants and gaseous phase pollutants. The particle phase pollutants are pollutants with significant physical sizes including dust particles, airborne bacteria and mold. They may be composed and be bound together by different matters with different compositions. The gaseous phase pollutants are pollutants with simple chemical structures. The size of the gaseous phase pollutants are small from angstrom to nano-scale.

There are many methods to eliminate the particle phase pollutants or pollutants with significant physical sizes. Conventionally, a High-Efficiency Particulate Arresting filter (HEPA filter) is used to filtrate particulate matter from the polluted air. On another hand, some may utilize a high-voltage to produce an electrostatic effect for dust removal. Some may release negative ion to the ambient, which eventually charges up the dust particulate, and allows them be collected in some regions which are relatively neutral or positively charged.

The efficiency and performance of using HEPA filter for dust removal is always better than that of the dust removal by the ionization or by the electrostatic precipitation methods. Nevertheless, the HEPA filter is a consumable item and cannot be recycled. It induces a high airflow resistant when the air is passing through it. When an air purifier integrated with HEPA filter, a fan with motor of relative large torque is usually needed in order to compensate the high airflow resistant that induced. It is not a environmental friendly method as more energy need to be consumed.

The air resistance induced by the electrostatic dust removal or particulate precipitation methods with the high-voltage component is usually low. To further improve the performance and efficiency of dust removal by a high-voltage component, higher operation voltage is usually employed. Though the operation current of the high-voltage is usually low, increasing of the operation voltage of the high-voltage component will lead to a high power consumption, which is not environmental friendly. In the past, many inventions disclosed special circuit design for the purpose to improve the performance of the high-voltage component for the electrostatic precipitation. Increase the operation voltage of the high-voltage component or decrease the distance between the positive and negative components of the electrostatic precipitator can generally help to improve the performance and efficiency of the dust removal. However, harmful ozone may be released as a side-product by these methods. On another hand, more strict regulations and requirements are imposed on the air purifier where high-voltage electrostatic precipitator for the safety concerns, which as a result, lower the flexibility and freedom on the design for the air purifier or air purification system. It is therefore difficult for designer of air purifier product to made the volume of air purifier small and compact.

Chinese utility model ZL200820120906.7 discloses an air purifier with high-voltage electrostatic precipitation component, where needle-shape charger is passing through the cylindrical electrostatic hollow collectors is disclosed. The invention reveals a one dimension, unidirectional and forwarding airflow path design. In order to increase the efficiency, very long cylindrical electrostatic hollow collectors are needed. Nevertheless, when the long cylindrical electrostatic hollow collectors occupied fully with dirty dust and particulates after used, the user would find the maintenance works become very annoyed and not convenience. The need of long cylindrical electrostatic hollow collectors would also lower the flexibility on air purifier design.

French patent FR 2623424 (A1) discloses that downstream of an ionization mean, a metal device for trapping the ionized particles by an electrostatic effect is installed. The metal device is curvature in shape and it is in perpendicular with the direction of the airflow. The airflow paths are allowed to be changed within a 2 dimensional planar orientation when come across the metal device, and hence the dust removal efficiency is therefore improved. Nevertheless, the process of fabrication of the metal device into this particular curvature shape during manufacturing is costly and complicated. Same as the mentioned Chinese utility model (Utility Patent No.: ZL200820120906.7), the maintenances works by the user after used are inconvenience as there are too many hidden curvature surface within the dust collector.

SUMMARY OF THE INVENTION

To solve the shortcoming present in the conventional air purification method, the present invention provides an innovative and new method and device for separate purifying the particulates from the air and/or the fluid. The said method and device is particularly suitable and applicable in air purification system. The present invention and device having the distinguishable features of (1) inducing low air flow resistance toward the whole air purifying system during particulates filtration, removal, precipitation, and reduction; (2) allows the precipitation of the particulates by the method of electrostatic to be operate with a high-voltage component and circuit, whereas the power consumption and the operation voltage of this said high-voltage component are at lower values when comparing to that of the conventional electrostatic precipitator for particulates of the same dimension. Same or even better performance and effectiveness on particulates removal can be obtained by the present invention; (3) allows the precipitation of the particulates by the method of electrostatic to be operate at a lower airflow rate when compare to that of the conventional electrostatic precipitator for particulates of the same dimension; and the same or even shorter time would be needed to achieve the pollutant level reduction in the area being concerned. Due to the mentioned distinguishable features, a blower or exhaust fan with motor of low torque can be adopted in the air purification system. Hence, the noise level of the air purification system can also be reduced. As lower operation voltage is allowed in order to achieve the same particulate removal performance as that of the device with the same product dimension, as a result, the safety requirement on the length of the creepage distance for the air purifier of this type can be shortened. The shortened creepage distance means a more compact and higher flexibility on the product and system design are allowed. The present invention also makes the maintenance works of the electrostatic precipitator for particulates easy to be handled, when compare to the conventional one.

In the first preferred aspect, there is providing an air purification device/system, comprising a casing; at least one air inlet; at least one air outlet defined in the casing; and at least one high-voltage electrostatic precipitator housed within the casing positioned between the at least one air inlet and the at least one air outlet, the at least one high-voltage electrostatic precipitator including a plurality of overlapping layers, each layer including a first linear housing section, and a second linear housing section that is angularly connected to the first linear housing section by a first parabolic curve formed therebetween, and a third section that is angularly connected to the second linear housing section of a first layer and the second linear housing section of a second layer adjacent to the first layer and forms a second parabolic curve by a U-shaped component, longitudinal directions of the first linear housing section and the second linear housing section being non-parallel with each other, the at least one high-voltage electrostatic precipitator including at least one positively charged component having positively charged top and bottom metal plates, the first and second linear housing sections being sandwiched by the positively charged top and bottom metal plates, side walls of the first and second linear housing sections being continuously connected sections in an air flow direction and forming a curvature that corresponds to the first parabolic curve. Air with particulates in an air stream flows from an upstream position to a downstream position between the at least one air inlet and the at least one air outlet of the air purification system through the first linear housing section, the second linear housing section and the third section of the at least one high-voltage electrostatic precipitator, and particulate matter contained in the air is collected by a component of the at least one high-voltage electrostatic precipitator. A direction of an airflow path of the air with particulates changes twice within the at least one high-voltage electrostatic precipitator, in a manner alternatively between the angularly connected first and second linear housing sections, and the third section, according to (a) first, through the first and second linear housing sections of the at least one high-voltage electrostatic precipitator, the direction of the airflow changes within a horizontal planar orientation defined by an x-axis and a y-axis; and (b) second, through the second linear housing section and the third section of the at least one high-voltage electrostatic precipitator within a vertical orientation defined by a z-axis, the direction of the airflow path changes in a direction unparallel with the horizontal planar orientation. The first parabolic curve between the first linear housing section and the second linear housing section of each layer curves with a same curvature as a curvature of the first parabolic curve in other layers. The direction of the airflow path of the air in (a) the first linear housing section, (b) the first parabolic curve and (c) the second linear housing section of the first layer and the direction of the airflow of the air in an adjacent layer are opposite from each other.

Figure 1:
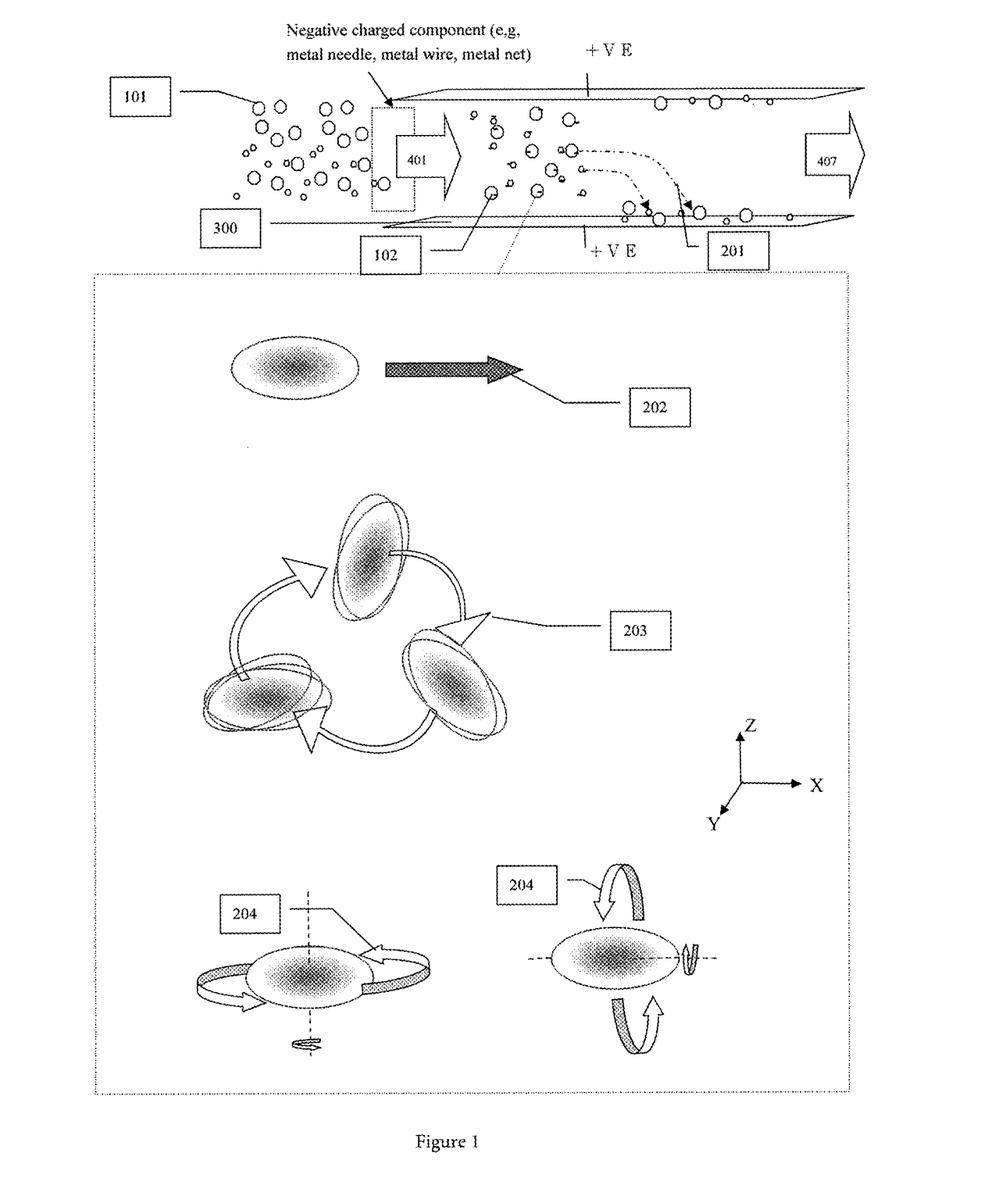
FIG. 1 illustrated the airflow of the negatively charged particulates is traveling in a direction of parabolic curve manner, three dimensional self-spinning manner, and three dimensional rotational manner.

When the positively charged component of the electrostatic precipitator is arranged as a long passage, and when the negatively charged particulates is passing through this long passage, the negatively charged particulates will be attracted toward the surface of the positively charged component, whereas it in a parabolic traveling path (as indicated in FIG. 1). The path is based on the mass-charge ratio of the charged particulates. If the particulates, after passing this long passage, and still not be attracted and attached onto the positively charged component, it would probably due to the following reason(s):

(a) The length of the passage of the positively charged component is too short;
(b) The air flow rate is too fast, and so as the velocity of the negatively charged particulates;
(c) The voltages different of the positively charged component and the negatively charged components is not high enough, as a result, the particulates matter do not carried enough negatively charges for being attract to the positively charged component, or the positively charged component does not have enough affinity to attract the negatively charged particulates;
(d) The weight of the negatively charged particulates matter is too heavy, and the momentum of the forwarding velocity is too high, the positively charged component does not have enough gravitational and or attraction force to change the direction of the path of the negatively charged particulates.

To enhance the effectiveness of the particulates precipitation and to prevent the causes of the problem as mentioned above, the following designs could be adopted.

(1) To increase the length of the passage of the positively charged component for the air (or negatively charged particulates) to passing through it
(2) To decrease the velocity of the air flow within the positively charged component
(3) To increase the operation voltage difference between the positively charged and negatively charged components.

As (3) increasing the operation voltage different between the positively charged component and negatively charged components will further lead to harsher product requirement in order to meet the safety regulation for high-voltage components, it would not be considered as an effective way to solve the shortcoming of the conventional method. In opposite, the improvement method stated in (1) and (2) of the above become the objectives for further improve the performance and effectiveness of the particulates removal by the electrostatic precipitation in the present invention.

In the present invention, when the air flows within the electrostatic precipitator, the direction of the path of the airflow changes at least twice. This would increase the length of the passage for the charged particulates when the air stream through it. It can also further lead to the following positive effect:

(1) every time when the direction of the airflow path changes, the velocity of the airflow, as well as the particulates in the air stream become lowered. The 3-dimensional velocities and 3-dimensional momentum of the negatively charged particulates thus, is reduced. The said 3-dimensional velocities are referring to (i) the forwarding velocity of the negatively charged particulates; (ii) the 3-dimensional self spinning velocity; (iii) and the 3-dimensional revolute velocity. The 3-dimensional momentum is referring to the energy aroused by the 3-dimensional velocities. As the momentum of the negatively charged particulates is lowered, the negatively charged particulates become more easily to be attracted to the surface of the positively charge component. FIG. 1 indicated the different way of motion of the negatively charged particulates in the air stream: (i) traveling forward; (ii) self-spinning and (iii) in a revolution manner against an external axis.
(2) During the first changing of the direction of the airflow (i.e., airflow is changed within a planar orientation or within a horizontal surface, by changing the x-axis— the y-axis coordinate of the airflow path in an x-y plane), partial or total of the negatively charged particulates would have their the translational velocity being slowed down, after bombarded on some obstacle object. Some of the negatively charged particulates may even become self-spinning against it central axis or turning around in a rotational manner against an external axis. The said obstacle object includes (a) those negatively charged particulates, where they were slowed down already but not yet been attracted to the positively charge component; (b) the turbulent airflow, which was created after the airflow bombarded on the surface of the positively charged component. The lowering of the translational velocity of the negatively charged particulate would enhance the changes of their attraction toward the surface of the positively charged component.

(3) By the law of inertia, the particulates are always tending to move forward following the air stream, without an external un-balance force. When a positively charged component with a bend in shape (or the positively charged component is not a planar object; or the positively charged component is a 3-dimensional orientated object) is utilized and when the direction of the airflow path is forced and is guided to change due to the said bending shape or orientations of the positively charge component or its structures, the negatively charged particulates would then bombard on and be attracted and attached on the surface of the positively charged component.

(4) The air inlet is in a upper position when compare to that of the air outlet. Every time when the direction of the airflow path is force to change in a vertical position (changing the x and z coordinates or y and z coordinates against the x-z plane or y-z plane of the airflow path), the potential energy of the negatively charged particle would be consumed. The consumption of the energy of the negatively charged particulate, again, enhance their attraction toward the positively charge component.

In order to prevent "short-circuit" of the airflow path, i.e., to prevent the cleaned air being drawn from air-outlet immediately to re-enter to the electrostatic precipitator through the nearby air-inlet, the said air inlet and air outlet are preferred be arranged in the following aspect: when the air-outlet and air-inlet of the electrostatic precipitator are closed and next to each other, relative to the airflow path and orientation at the air inlet, the airflow path and orientation of the air outlet has an angle of at least 30° against that of the air inlet.

The air and fluid which are to be cleaned includes any those from the respirable suspended particulate matter, particulate matter of any sizes, PM10 (particulate matter of size in 10 micron), PM2.5 (particulate matter of size in 2.5 micron), the smoke generated from a burning cigarette, environmental tobacco smoke, and airborne bacteria.

While changing the direction of the airflow path twice within an air purification device/system, the changed of the said directions in fact are guided by the shape, orientation, alignment and arrangement of the of the positively charged components where the airflow stream within it.

The said air purification device/system, further comprise at least one filtration component other than the said high-voltage electrostatic precipitator, for purifying and/or filtering the particle phase and gases phase pollutants. The said filtration component can be installed upstream, downstream or even in the same level in series with the said high-voltage electrostatic precipitator. The said filtration component comprises at least one of the follows:

(a) pre-filter for filter the large size particle;
(b) pellet form of activated carbon materials, photo catalytic materials or molecular sieve materials, and/or pellet mixtures of any of the above mentioned materials; the pellet materials are put in a container which is permeable for air to pass through it; the materials are acting as carrier for gases phase pollutants during filtration;
(c) materials attached with activated carbon, photo-catalyst or molecular sieve, and/or mixtures of any of the above mentioned materials; the said materials is permeable for air to pass through it and can remove the gases phase pollutants during the filtration;
(d) honeycomb structure where it contains the materials of activated carbon, photo-catalyst or molecular sieve, and/or mixtures of any of the above mentioned materials;
(e) High-Efficiency Particulate Arresting filter (HEPA filter);
(f) Germicidal section by mean of Ultra-Violet light The air purification device/system further comprises a device and/or method for driving the airflow stream from upstream to the downstream. The said device for driving the airflow stream from upstream to the downstream can be any or the combination of a fan, a blower, or air re-circulation devices. The said method for driving the airflow stream from upstream to the downstream comprises connecting the said air purification device/system to an environmental device, which the environmental device is equipped with a fan or a blower. The way of connection can be performed by connecting partial or all of the air inlet and/or air outlet of the air purification device/system to the air inlet and/or air outlet of the said environmental device.

The air purification device/system comprise further at least one exhaust fan which is installed at the downstream position of the air purification device/system.

The air purification device/system comprise further at least one blower which is installed at the upstream position of the air purification device/system.

The air purification system comprise a high-voltage electrostatic precipitator, wherein the electrostatic precipitator is 2-dimensional planar metallic or conductive object which is positively charged; the 2-dimensional planar object is a plain surface or a surface with up and down waveform shape for increasing the total surface area for dust collection. The 2-dimensional planar object is connected to the positive voltage terminal. The 2-dimensional planer object fabricated by metal materials or any materials that is electrically conductive. More than one 2-dimensional planar object is connected together by connecting component (e.g., connecting component in U-shape) and formed a 3-dimensional object. The direction of the airflow path changed at least twice when it is streamed within the 3-dimensional object. The connecting component is preferred to be made of metal or conductive materials.

The high-voltage electrostatic precipitator comprises a negatively charged component with the following features:

(a) The negatively charged component comprises metal needle(s) or conductive materials which are in needle shaped and being connected to the negative voltage terminal;
(b) The negatively charged component comprises metal wire(s) or conductive materials which are in wire shaped and being connected to the negative voltage terminal;

(c) The negatively charged component comprises metal net (s) or conductive materials which are in net shaped and being connected to the negative voltage terminal;
(d) The negatively charged component comprises at least two of the any above mentioned features.

The air purification device/system further comprises a high-voltage electrostatic precipitator, wherein the positively charged components are equipped at the downstream position of the negatively charged components.

The air purification device/system further comprises a high-voltage electrostatic precipitator, wherein the positively charged components are aligned parallel to the negatively charged components, and also parallel to the direction of the airflow path.

The air purification device/system further comprises a high-voltage electrostatic precipitator, wherein the positively charged components are interlaced parallel to the negatively charged components in a single or multiple "sandwiching" manners. As the airflow is passing though a paralleled positively charged passage which is of even thickness, high frequent noise which induced by the cyclone style electrostatic precipitator will not be generated.

The air purification device/system further comprises a high-voltage electrostatic precipitator, wherein the positively charged components are replaced by:
(a) a neutral charged component;
(b) another negatively charged component but with relatively lower voltage value, when compared to the negatively charged components of the original electrostatic precipitator.

The present invention further comprises a method for air purification, which are implemented by any of the above mentioned technique.

The air purification system/device present in the present invention can also be interpreted as a standalone electrostatic precipitator unit which is applicable to be installed in any different type of air purification device/system/system. The air inlet refers to the air inlet of the standalone electrostatic precipitator unit, whereas the air outlet refers to the air outlet of the standalone electrostatic precipitator unit.

BRIEF DESCRIPTION OF THE DRAWING

FIG. 3 illustrated the outlook of the positively charge components for particulates collection FIG. 4 illustrated when the air inlet and air outlet of the high-voltage electrostatic precipitator is in neighborhood with each other, the orientation and angle separation between for airflow them shall more than 30°.

DETAILS DESCRIPTION OF THE DRAWING

FIG. 1 indicates the particulates pollutants 101 flows via an airflow 401 traveling in a forward direction. When the airflow passes through the negatively charged components, the particulate pollutants will be charged up and become the negatively charged particulates 102. On passing through the passage of the positively charged component 300 of the electrostatic precipitator, the negatively charged particulates 102 will travel according to a parabolic curve 201 and be attached to the surface of the positively charged component 300 according the mass to charge ratio of them. Besides the traveling in a forwarding direction 202 with a translational velocity, the negatively charged particulates also moving in with the direction which is rotating in a turning around manner 203, self-spinning manner against the x-y axis 204a, self-spinning manner against the z-y axis 204b, self-spinning manner against the x-z axis 204c. When the airflow 401 is passing through the positively charged component of the electrostatic precipitator, the direction of the airflow 401 path changes at least twice, wherein, the velocities of the different rotating and self-spinnings 203, 204a, 204b, 204c are lowered. As a result, the total momentum of the negatively charged particulates 102 is reduced. The negatively charged particulates 102 become easily be attracted and attached on the surface of the surface of the positively charged component 300.

In one embodiment, when the direction of the airflow path change (i.e., the direction of the airflow path is changing planar in a x-y axis surface), partial or total negatively charged particulates 102 bombarded on the obstacle object and have their translational velocity 202 (which is in a forward direction) be slowed down. Some of the translational velocity 202 will transformed to angular velocities 203 & 204a, 204b, 204c as the particulates matter become spinning and turned around after bombard on the obstacle object. As the translational velocity 202 of the negatively charged particulates 102 is lowered, it is then more easily to be attracted and be attach on the surface of the positively charge components. Upon changing the direction of the airflow again in a vertical (up and down) manner (direction relative to the original x-y planar orientation), the original translation velocity and angular velocities 203 & 204a, 204b, 204c will further be slowed down. The original spinning and rotation directions will change to other ways of spinning and rotation. All these changed the velocities of the negatively charged particles and make it become more easily to be caught by the positively charged component during the electrostatic precipitation.

Figure 2:
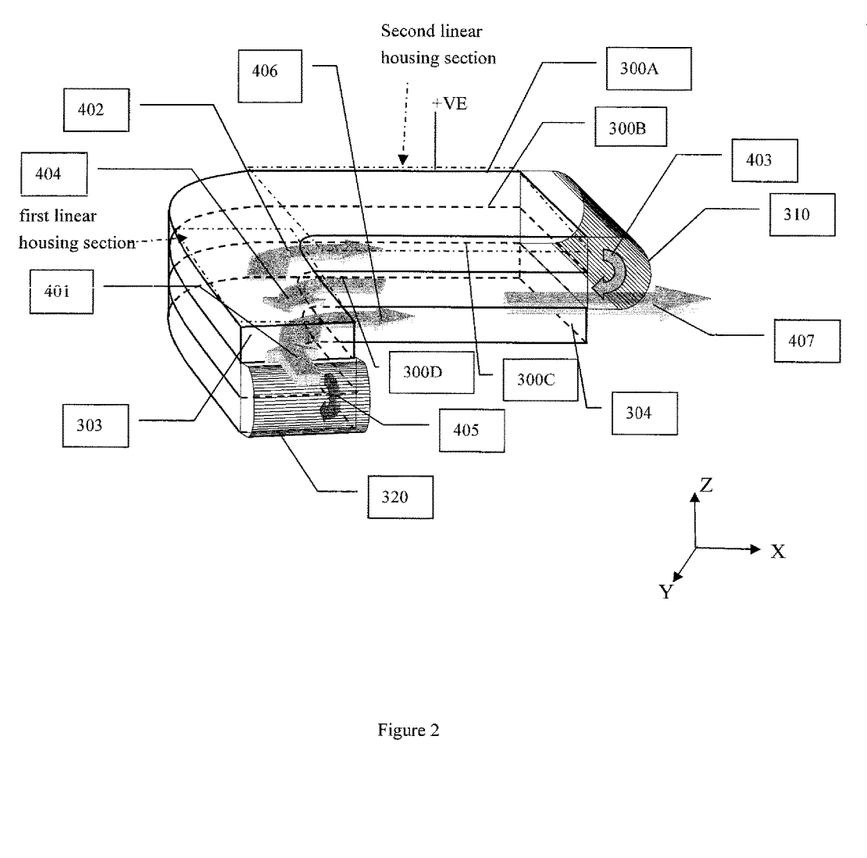
FIG. 2 illustrated the internal structure of the high-voltage electrostatic precipitator of in the present invention.

FIG. 2 indicates in another embodiment, the structure of the high-voltage electrostatic precipitator for air purification system is presented. Four planar metal plate or conductive materials 300 with shape as shown are put together in an overlapping manner into a three dimensional volume. The layers are in sequence of 300A-300B-300C-300D. Each layer is separated with 15 mm distance apart. One end of the first layer metal plate 300A and one end of the third layer metal plate 300C are connected together by a U-shaped connecting component 310. Another end of the second layer metal plate 300B and another end of the fourth layer metal plate 300D are connected together by another U-shaped connecting component 320. In between each layer of the planar metal plate or conductive materials, the negatively charged components are interlaced in a parallel manner, wherein, the distance between the upper layer metal plate and the negatively charged component are equal to that between the lower layer metal plate and the negatively charged component, in order to prevent the localized voltage breakdown, which would otherwise induce sparks during the high voltage operation. The said negatively charged component comprises the conductive wires which are in connection with the negative voltage terminal (while in other embodiment, the conductive net or needle object might be used as the negatively charged component). In the present embodiment, the voltage value is adjustable according to need during operation. It can be adjusted between 2K volt to 6K volt. The airflow is then steam within the high-voltage electrostatic precipitator as the following path:

(1) The uncleaned airflow 401 from the environment enter the high-voltage electrostatic precipiator through the air inlet 303, it flows in between the metal plate layers 330A and 300B. The negatively charged particulates within the airflow 401 is then be attracted and attached on the surface of the positively charged component. When flowing within the spacing between the metal plate layers 300A and 300B, the direction of the airflow path changed once, which is planar manner 402, i.e., the coordinates of x-axis and y-axis of the airflow path changed.

(2) When airflow flow to the U-shaped connecting component 310, the direction of the airflow path changes again 403. The direction of the airflow path is changing vertically between a upper and lower locations, i.e., the coordinates in x-z axis and y-z axis of the airflow path changed 403.

(1) When the airflow turn to stream between the second 300B and third 300C positively charged metal layers, the direction of the airflow path changed once again, which is in a planar manner 404;

(4) When airflow flow to the U-shaped connecting component 320, which connecting another end of the second 300B and forth 300D layer of the positively charged component, the direction of the airflow path changes the forth time. The direction of the airflow path is changing vertically between a upper and lower locations, i.e., the coordinates in x-z axis and y-z axis of the airflow path changed 405;

(5) When the airflow turn to stream between the third 300C and forth 300D positively charged metal layers, the direction of the airflow path changed once again, which is in a planar manner 406;

(6) Finally, the cleaned airflow 407 exist the 3-dimension volume of the positively charge component 304 and be exhausted.

If U-shaped connecting component is made of metal or or other conductive materials, the performance will be come even more significant.

In the present embodiment, the air inlet 303 of the high-voltage electrostatic precipitator is located at a higher position in compare to the air outlet 304. In opposite, if their position is reverse in a way that if the air inlet 303 is located at a lower position than the air outlet 304, then the potential energy of the negatively charged particulate will further be consumed when the airflow path is turning up each time when it mean the U-shaped connecting component. The particulate removal performance by the high-voltage electrostatic precipitator can further be enhanced.

Figure 3:
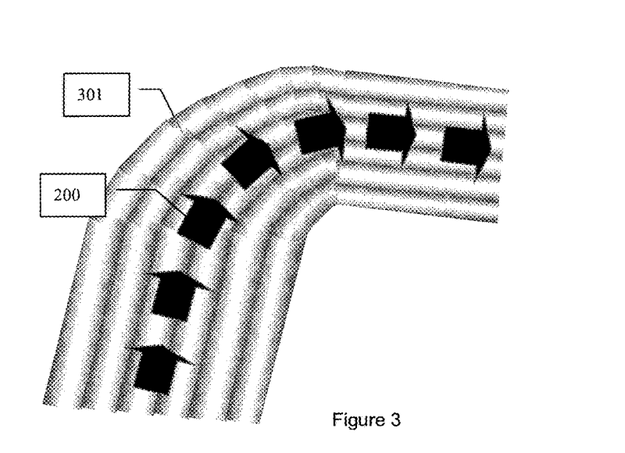

FIG. 3 indicated the morphology of the positively charged component which is connecting to the positive voltage terminal of the high-voltage electrostatic precipitator. The positively charged component is fabricated with conductive materials or metal with up and down waveform surface 301. The waveform morphology greatly increases the area for dust collection. The shape of the waveform shall be parallel with the airflow path 200. The waveform can also be turned or bended according to the outlook of the positively charged component as shown.

Figure 4:
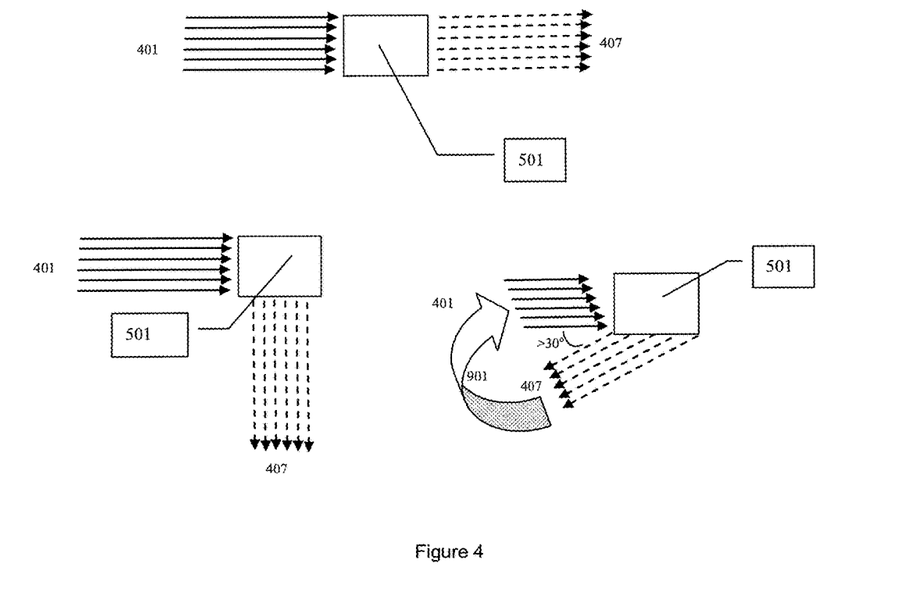

FIG. 4 indicated the when the air inlet 303 and air outlet 304 of the high voltage electrostatic precipitator 501 is in neighborhood with each other, the angle and orientation of the airflow path 407 of from the air outlet 304 and that from the air inlet 303 shall be greater than 30°. This is to prevent the short-circuit 901 of the airflow. More specifically, this prevent the cleaned air exhaust from the outlet immediately be drawn into the air-inlet where the un-cleaned air from the environment cannot approached to the air-inlet due to the airflow short-circuit.

Figure 5:
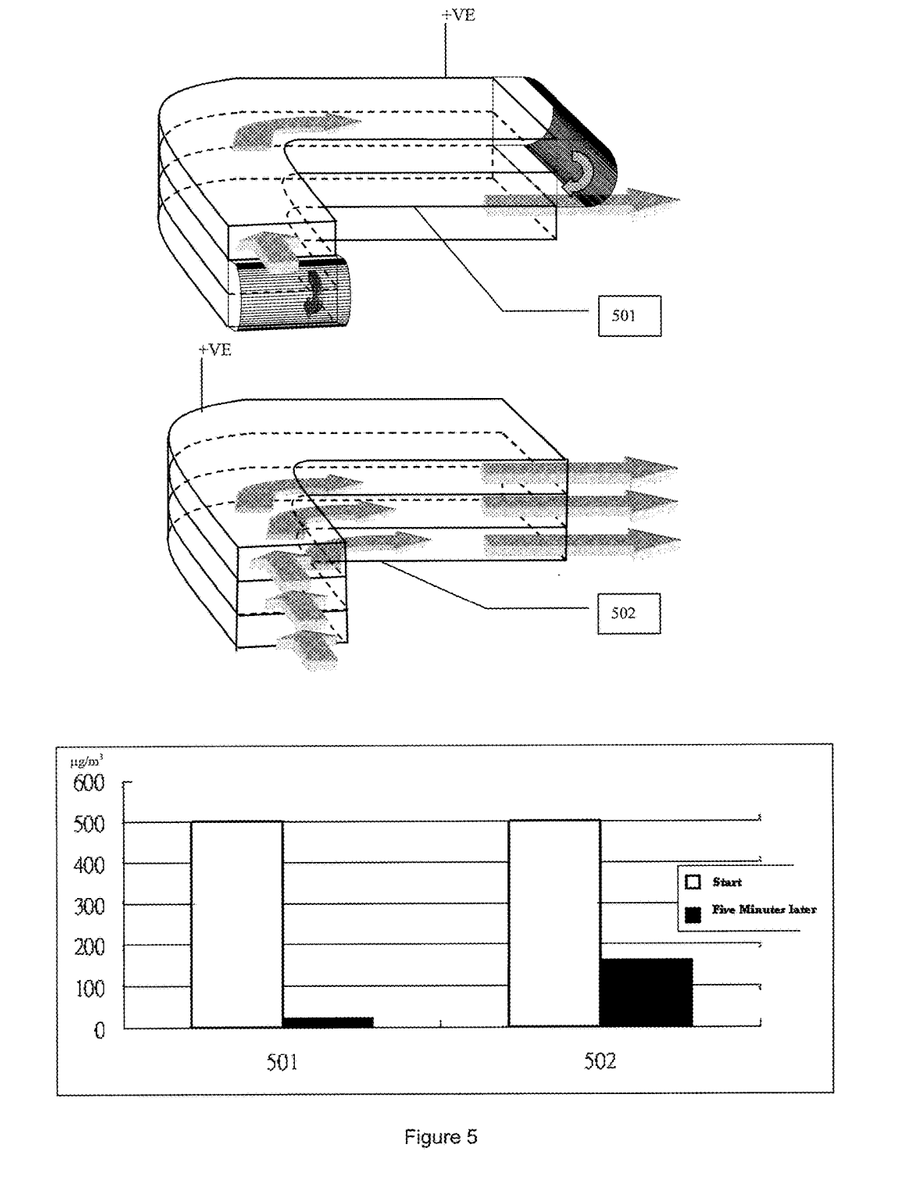
FIG. 5 illustrated comparison on the performance of the particulates removal on (1) a high-voltage electrostatic precipitator device where the direction of the airflow path changes at least twice as mentioned in the present invention; (2) a high-voltage electrostatic precipitator where the direction of the airflow path changes once only.

FIG. 5 illustrated comparison on the performance of the particulates removal on (1) a high-voltage electrostatic precipitator device where the direction of the airflow path changes at least twice as mentioned in the present invention 501; (2) a high-voltage electrostatic precipitator where the direction of the airflow path changes once only 502. The high-voltage electrostatic precipitator 502 does not contain any U-shaped connecting component at each end as the embodiment explained in FIG. 2. The high-voltage electrostatic precipitator 501 has a longer passage for negatively charged particulate in comparing to the high-voltage electrostatic precipitator 502. When the two high-voltage electrostatic precipitator are put into two air purification system with same parameters (same airflow rate and same operating voltage for the electrostatic precipitator), they can performed differently. For example, when they are put into two room of size 1 m×2 m×4 m where the pollutant PM10 was in a level of 500 □g/m$^3$, the high-voltage electrostatic precipitator 501 is capable to reduce the pollutant level to 25 □g/m$^3$, where the electrostatic precipitator 502 can only reduce it up to 160 □g/m$^3$. The present invention can help to enhance the removal efficiency for particulate matter. In other word, it can help to increase the Clean Air Delivery Rate (CADR) under the same airflow rate. Similar performance are also found if the study is substituted with particulate matter of size 2.5 micron (PM2.5), pollen, smoke generated from cigarette and the environmental tobacco smoke.

It will be appreciated by person skilled in the art that numerous variation and/or modification may be made to the invention as shown in the specific embodiments without departing from the scope or spirit of the invention as broadly described. The present embodiment, are therefore, to be considered in respects illustrative and not restrictive.

The invention claimed is:

1. An air purification system, comprising:
    a casing;
    at least one air inlet;
    at least one air outlet defined in the casing; and
    at least one high-voltage electrostatic precipitator housed within the casing positioned between the at least one air inlet and the at least one air outlet, the at least one high-voltage electrostatic precipitator comprising:
        a plurality of overlapping layers, each layer including a first linear housing section, and a second linear housing section that is angularly connected to the first linear housing section by a first parabolic curve formed therebetween, and
        a third section that is angularly connected to the second linear housing section of a first layer and the second linear housing section of a second layer adjacent to the first layer and forms a second parabolic curve by a U-shaped component, longitudinal directions of the first linear housing section and the second linear housing section being non-parallel with each other, the at least one high-voltage electrostatic precipitator including at least one positively charged component having positively charged top and bottom metal plates, the first and second linear housing sections being sandwiched by the positively charged top and bottom metal plates, side walls of the first and second linear housing sections being continuously connected sections in an air flow direction and forming a curvature that corresponds to the first parabolic curve, wherein air with particulates in an air stream flows from an upstream position to a downstream position between the at least one air inlet and the at least one air outlet of the air purification system through the first linear housing section, the second linear housing section and the third section of the at least one high-voltage electrostatic precipitator, and particulate matter contained in the air is collected by a component of the at least one high-voltage electrostatic precipitator, wherein, a direction of an airflow path of the air with particulates changes twice within the at least one high-voltage electrostatic precipitator, in a manner alternatively between the angularly connected first and second linear housing sections, and the third section, according to:

(a) first, through the first and second linear housing sections of the at least one high-voltage electrostatic precipitator, the direction of the airflow changes within a horizontal planar orientation defined by an x-axis and a y-axis; and (b) second, through the second linear housing section and the third section of the at least one high-voltage electrostatic precipitator within a vertical orientation defined by a z-axis, the direction of the airflow path changes in a direction unparallel with the horizontal planar orientation, wherein the first parabolic curve between the first linear housing section and the second linear housing section of each layer curves with a same curvature as a curvature of the first parabolic curve in other layers, and wherein the direction of the airflow path of the air in (a) the first linear housing section, (b) the first parabolic curve and (c) the second linear housing section of the first layer and the direction of the airflow of the air in an adjacent layer are opposite from each other.

2. The air purification system according to claim 1, wherein the at least one high-voltage electrostatic precipitator further includes at least one negatively charged component which is connected to a negative voltage terminal, and the at least one positively charged component is connected to a positive voltage terminal.

3. The air purification system according to claim 2, wherein a change of the direction of the air flow path is guided by the orientation and shape of the internal structure of the at least one positively charged component of the at least one high-voltage electrostatic precipitator.

4. The air purification system according to claim 2, wherein the at least one negatively charged component is any one from the group consisting of:

(a) a negatively charged component comprises at least one metal needle or conductive materials which are in needle shaped and being connected to the at least one negative voltage terminal;

(b) a negatively charged component comprises at least one metal wire or conductive materials which are in wire shaped and being connected to the at least one negative voltage terminal;

(c) a negatively charged component comprises at least one metal net or conductive materials which are in net shaped and being connected to the at least one negative voltage terminal; and (d) a negatively charged component comprises at least two of the any above mentioned features.

5. The air purification system according to claim 2, wherein the at least one positively charged component of the at least one high-voltage electrostatic precipitator is located at a downstream position of the at least one negatively charged component.

6. The air purification system according to claim 2, wherein the at least one positively charged component are aligned parallel to the at least one negatively charged component.

7. The air purification system according to claim 2, wherein the at least one positively charged component is interlaced parallel to the at least one negatively charged component in a single or multiple sandwiching manner.

8. The air purification system according to claim 1, wherein the position of the at least one air outlet is located at a lower altitude position in comparison to that of the at least one air inlet.

9. The air purification system according to claim 1, further comprising at least one filtration component for further purifying and/or filtering particle phase and gases phase pollutants; the at least one filtration component either be installed upstream, downstream or in the same level in a series manner with the at least one high-voltage electrostatic precipitator.

10. The air purification system according to claim 1, further comprising any one from the group consisting of: a blower, an exhaust fan, and an air-recirculation device, for driving the airflow stream from upstream to the downstream.

11. The air purification system according to claim 1, wherein the air purification system is connected to an environmental device which is equipped with a fan or a blower; and the at least one air inlet and/or the at least one air outlet is at least partially connected to the at least one air inlet and/or the at least one air outlet of the environmental device.

12. The air purification system according to claim 1, wherein the at least one high-voltage electrostatic precipitator further comprises at least one positively charged 2-dimensional metallic or conductive planar object; the at least one positively charged 2-dimensional metallic or conductive planar object a substantially flat surface with either a plain surface or a waveform-shaped morphology on the substantially flat surface.

13. The air purification system according to claim 12, wherein at least two 2-dimensional metallic or conductive planar objects are connected together by at least one connecting component into a 3-dimensional metallic or conductive object.

14. The air purification system according to claim 13, wherein the at least one connecting component are metallic or conductive materials.

15. The air purification system according to claim 1, wherein the airflow path and orientation of the at least one air outlet has an angle of at least 30° against that of the at least one air inlet.

16. The air purification system according to claim 1, wherein the at least one high-voltage electrostatic precipitator further comprises at least one first negatively charged component and at least one second component, wherein the at least one second component comprises either:
  a neutrally charged component; or
  a negatively charged component with a lower voltage value compared to the at least one first negatively charged component.

* * * * *